US010555939B2

(12) United States Patent
Tutino et al.

(10) Patent No.: US 10,555,939 B2
(45) Date of Patent: *Feb. 11, 2020

(54) FORMULATIONS OF 4-AMINO-2-(2,6-DIOXOPIPERIDINE-3-YL)ISOINDOLINE-1,3-DIONE

(71) Applicant: Celgene Corporation, Summit, NJ (US)

(72) Inventors: Anthony J. Tutino, New Providence, NJ (US); Michael T. Kelly, Lake Hopatcong, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/976,808

(22) Filed: May 10, 2018

(65) Prior Publication Data
US 2018/0325885 A1 Nov. 15, 2018

Related U.S. Application Data

(63) Continuation of application No. 14/998,262, filed on Dec. 23, 2015, now Pat. No. 9,993,467, which is a continuation of application No. 14/447,450, filed on Jul. 30, 2014, which is a continuation of application No. 12/783,390, filed on May 19, 2010, now Pat. No. 8,828,427.

(60) Provisional application No. 61/179,678, filed on May 19, 2009.

(51) Int. Cl.
A61K 31/454 (2006.01)
A61K 47/10 (2017.01)
A61K 47/14 (2017.01)
A61K 47/26 (2006.01)
A61K 47/36 (2006.01)
A61K 9/48 (2006.01)

(52) U.S. Cl.
CPC .......... A61K 31/454 (2013.01); A61K 9/4858 (2013.01); A61K 9/4866 (2013.01); A61K 47/10 (2013.01); A61K 47/14 (2013.01); A61K 47/26 (2013.01); A61K 47/36 (2013.01); Y02A 50/409 (2018.01); Y02A 50/411 (2018.01)

(58) Field of Classification Search
CPC ............................. A61K 31/454; A61K 9/4858
See application file for complete search history.

(56) References Cited

U.S. PATENT DOCUMENTS

| 3,145,146 | A | 8/1964 | Lieberman et al. |
|---|---|---|---|
| 3,980,766 | A | 9/1976 | Shaw et al. |
| 4,551,177 | A | 11/1985 | Trubiano et al. |
| 4,713,247 | A | 12/1987 | Sakamoto et al. |
| 4,906,647 | A | 3/1990 | Kouchiwa et al. |
| 5,385,901 | A | 1/1995 | Kaplan et al. |
| 5,593,696 | A | 1/1997 | McNally et al. |
| 5,594,637 | A | 1/1997 | Eisenberg et al. |
| 5,619,991 | A | 4/1997 | Sloane |
| 5,635,517 | A | 6/1997 | Muller et al. |
| 5,712,291 | A | 1/1998 | D'Amato |
| 5,731,325 | A | 3/1998 | Andrulis, Jr. et al. |
| 5,798,368 | A | 8/1998 | Muller et al. |
| 5,832,449 | A | 11/1998 | Cunningham |
| 5,882,656 | A | 3/1999 | Bechard et al. |
| 5,974,203 | A | 10/1999 | Tadokoro et al. |
| 6,045,501 | A | 4/2000 | Elsayed et al. |
| 6,055,507 | A | 4/2000 | Cunningham |
| 6,063,026 | A | 5/2000 | Schauss et al. |
| 6,131,090 | A | 10/2000 | Basso et al. |
| 6,202,923 | B1 | 3/2001 | Boyer et al. |
| 6,281,230 | B1 | 8/2001 | Muller et al. |
| 6,315,720 | B1 | 11/2001 | Williams et al. |
| 6,316,471 | B1 | 11/2001 | Muller et al. |
| 6,476,052 | B1 | 11/2002 | Muller et al. |
| 6,555,554 | B2 | 4/2003 | Muller et al. |
| 6,561,976 | B2 | 5/2003 | Elsayed et al. |
| 6,561,977 | B2 | 5/2003 | Williams et al. |
| 6,703,424 | B2 | 3/2004 | Levin et al. |
| 6,755,784 | B2 | 6/2004 | Williams et al. |
| 6,878,733 | B1 | 4/2005 | Shenoy et al. |
| 6,896,399 | B2 | 5/2005 | Nomura et al. |
| 6,908,432 | B2 | 6/2005 | Elsayed et al. |
| 7,119,106 | B2 | 10/2006 | Muller et al. |
| 7,125,565 | B2 | 10/2006 | Sugishita et al. |
| 7,189,740 | B2 | 3/2007 | Zeldis |
| 7,393,862 | B2 | 7/2008 | Zeldis |
| 7,465,800 | B2 | 12/2008 | Jaworsky et al. |

(Continued)

FOREIGN PATENT DOCUMENTS

| CA | 2712724 A1 | 8/2009 |
|---|---|---|
| EP | 1 884 242 B1 | 4/2013 |

(Continued)

OTHER PUBLICATIONS

"CDC meeting: Mar. 26, 1997 minutes and agenda regarding thalidomide.".
"Celgene's Revlimid an orphan drug, says FDA," Marketletter Oct. 15, 2001.
"Center for drug evaluation and research approval package for: Application No. 18-662/S-038," (2000).
"Center for drug evaluation and research approval package for: Application No. NDA 20-785 approval letter(s)," Sep. 19, 1997 and Jul. 16, 1998.
"EntreMed moves towards commercialization with production of thalidomide analogs; Next generation drug candidates to be manufactured in preparation for clinical studies," *PR Newswire* (2001).

(Continued)

Primary Examiner — Alma Pipic
(74) Attorney, Agent, or Firm — Jones Day

(57) ABSTRACT

Pharmaceutical compositions and single unit dosage forms of 4-amino-2-(2,6-dioxopiperidine-3-yl)isoindoline-1,3-dione, or a pharmaceutically acceptable stereoisomer, prodrug, salt, solvate, hydrate, or clathrate, are provided herein. Also provided are methods of treating, managing, or preventing various disorders, such as cancer or an inflammatory disease.

8 Claims, No Drawings

(56) References Cited

U.S. PATENT DOCUMENTS

| | | |
|---|---|---|
| 7,855,217 B2 | 12/2010 | Jaworski et al. |
| 7,959,566 B2 | 6/2011 | Williams et al. |
| 7,968,569 B2 | 6/2011 | Zeldis |
| 8,158,653 B2 | 4/2012 | Muller et al. |
| 8,188,118 B2 | 5/2012 | Zeldis |
| 8,198,262 B2 | 6/2012 | Zeldis |
| 8,198,306 B2 | 6/2012 | Zeldis |
| 8,204,763 B2 | 6/2012 | Elsayed et al. |
| 8,207,200 B2 | 6/2012 | Zeldis |
| 8,315,886 B2 | 11/2012 | Williams et al. |
| 8,530,498 B1 | 9/2013 | Zeldis |
| 8,589,188 B2 | 11/2013 | Elsayed et al. |
| 8,626,531 B2 | 1/2014 | Williams et al. |
| 8,648,095 B2 | 2/2014 | Zeldis |
| 8,673,939 B2 | 3/2014 | Zeldis |
| 8,735,428 B2 | 5/2014 | Zeldis |
| 8,828,427 B2 | 9/2014 | Tutino et al. |
| 9,101,621 B2 | 8/2015 | Zeldis |
| 9,101,622 B2 | 8/2015 | Zeldis |
| 9,993,467 B2 * | 6/2018 | Tutino et al. |
| 2002/0054899 A1 | 5/2002 | Zeldis et al. |
| 2004/0087546 A1 | 5/2004 | Zeldis |
| 2004/0191298 A1 | 9/2004 | Nicklasson et al. |
| 2007/0155791 A1 | 7/2007 | Zeldis et al. |
| 2008/0107731 A1 | 5/2008 | Kohlrausch et al. |

FOREIGN PATENT DOCUMENTS

| | | |
|---|---|---|
| EP | 1 886 678 B1 | 4/2017 |
| JP | H 0977669 A | 3/1997 |
| WO | WO 96/013790 | 5/1996 |
| WO | WO 98/013783 | 4/1998 |
| WO | WO 99/010829 | 3/1999 |
| WO | WO 00/44351 A1 | 8/2000 |
| WO | WO 00/051053 | 8/2000 |
| WO | WO 02/43720 A2 | 6/2002 |
| WO | WO 02/064083 | 8/2002 |
| WO | WO 2004/043377 A2 | 5/2004 |
| WO | WO 2004/045579 A2 | 6/2004 |
| WO | WO 2005/023192 A2 | 3/2005 |
| WO | WO 2005/072736 A2 | 8/2005 |
| WO | WO 2006/058008 A1 | 6/2006 |
| WO | WO 2006/097943 A2 | 9/2006 |
| WO | WO 2007/079182 A1 | 7/2007 |
| WO | WO 2009/097120 A1 | 8/2009 |
| WO | WO 2010/135396 A2 | 11/2010 |

OTHER PUBLICATIONS

Adams et al., "Proteasome inhibitors: A novel class of potent and effective antitumor agents," *Cancer Res.* 59:2615-2622 (1999).
Alder et al., "The return of thaliomide—A shunned compound makes a scientific comeback," *Science News* 146:424-425 (1994).
Alderborn, "Tablets and compaction," in Pharmaceutics: The Science of Dosage Form Design, M. Aulton (ed.), Elsevier Limited, Chapter 27, pp. 397-417 (2002).
Alexanian et al., "High-dose glucocorticoid treatment of resistant myeloma," *Ann. Intern. Med.* 105:8-11 (1986).
Alexanian et al., "Consolidation therapy of multiple myeloma with thalidomide-dexamethasone after intensive chemotherapy," *Ann Oncol.* 13:1116-1119 (2002).
Anderson et al., "Multiple myeloma: New insights and therapeutic approaches," *Hematology Am. Soc. Hematol. Educ. Program* 2000:147-165 (2000).
Anderson et al., "Novel biologically based therapies for myeloma," VIII the International Myeloma Workshop, Banff, Alberta, Canada, May 4-8, 2001; Abstract #S27.
Barlogie et al., "Effective Treatment of Advanced Multiple Myeloma Refractory to Alkylating Agents," *N. Engl. J. Med.*, 310(21):1353-1356 (1984).
Bauer et al., "Pharmazeutische Technologic," ["Pharmaceutical Technology"], 4$^{th}$ edition, p. 160 (1993).

Bjorkstrand et al., "Prognostic factors in autologous stem cell transplantation for multiple myeloma: an EBMT registry study," *Leuk. Lymphoma* 15:265-272 (1994).
Bor, "Thalidomide shows that it can heal, too from deformer of babies to force for good," *Baltimore Sun* (1995).
Brittain, "Overview of the solid dosage form preformulation program," in Preformulation in Solid Dosage Form Development, pp. 347-372 (2008).
Broder et al., "Dideoxycytidine: Current clinical experience and future prospects. A summary," *Am. J. Med.* 88:31S-33S (1990).
Burleson, "Review of computer applications in institutional pharmacy—1975-1981," *Am. J. Hosp. Pharm.* 39:53-70 (1982).
Bwire et al., Managing the teratogenic risk of thalidomide and lenalidomide: An industry perspective, *Expert Opin. Drug Saf.* 10:3-8 (2011).
Cairo, "Dose reductions and delays: Limitations of myelosuppressive chemotherapy," *Cancer Network* (2000).
Canal et al., "Benefits of pharmacological knowledge in the design and monitoring of cancer chemotherapy," *Pathology Oncol. Res.* 4:171-178 (1998).
Celgene Corporation Awarded Additional Patent Protection For Lead IMiD(TM), REVIMID(TM); Comprehensive Patent Protection for REVIMID Includes Coverage of the Active Ingredient, Pharmaceutical Compositions, and Therapeutic Uses PR Newswire Aug. 28, 2001.
Celgene Corporation, "Initial Phase I solid tumor data on Celgene's lead IMiD™, Revimid™," Press Release, Jun. 2001.
Celgene Corporation, Form 424B4 (2000).
Celgene News Release, "Positive interim results presented at the VIIIth international myeloma workshop on Celgene Corporation's lead IMiD™ (REV/MID™)," May 8, 2001.
Cheson, "New drug development in non-Hodgkin lymphomas," *Curr. Oncol. Rep.* 3:250-259 (2001).
Chu et al., "Principles of cancer management: Chemotherapy," in Cancer: Principles and Practice of Oncology, 6th edition, De Vita et al., (eds.), Lippincott Williams & Wilkins, Philadelphia, PA Chapter 17 (2001).
Corral et al., "Differential cytokine modulation and T cell activation by two distinct classes of thalidomide analogues that are potent inhibitors of TNF-α," *J. Immunol.* 163:380-386 (1999).
Corral et al., "Immunomodulation by thalidomide and thalidomide analogues," *Ann. Rheum. Dis.*, 58(Suppl 1):I107-I113 (1999).
Crane et al., "Immunomodulatory drugs," *Cancer Investigation* 23:625-634 (2005).
D'Amato et al., "Mechanism of action of thalidomide and 3-aminothalidomide in multiple myeloma," *Semin. Oncol.*, 28:597-601 (2001).
D'Amato et al., "Thalidomide is an Inhibitor of Angiogenesis," *Proc. Natl. Acad. Sci. USA*, 91(9):4082-4085 (1994).
Damaj et al., "Thalidomide therapy induces response in relapsed mantle cell lymphoma," *Leukemia* 17:1914-1915 (2003).
Dancey et al., "Neutrophil kinetics in man," *J. Clin. Invest.* 58:705-715 (1976).
Davies et al., "Thalidomide and immunomodulatory derivatives augment natural killer cell cytotoxicity in multiple myeloma," *Blood*, 98(1):210-216 (2001).
Declaration of Anthony Tutino, dated Jun. 14, 2013 in U.S. Appl. No. 12/783,390.
Devita et al., eds., "Plasma cell neoplasm." In *Cancer Principles & Practice of Oncology*, 5th Ed.; Lippincott-Raven Publishers, pp. 2344-2379 (1997).
Dimopoulos et al., "Thalidomide and dexamethasone combination for multiple myeloma refractory to dexamethasone-based reginens," *Blood* 96(Supp):286b (2000).
Dimopoulos et al., "Thalidomide and dexamethasone combination for refractory multiple myeloma," *Ann. Oncol.* 12:991-995 (2001).
Dishman et al., "Pharmacists'ranscript role in clozapine therapy at a veterans affairs medical center," *Am. J. Hosp. Pharm.* 51:899-901 (1994).
Drach et al., "Treatment of mantle cell lymphoma: Targeting the microenvironment," *Expert Rev. Anticancer Ther.* 5:477-485 (2005).
Durie and Stepan, "Efficacy of low dose thalidomide in multiple myeloma," *Eur. J. Oncol.* 1:1-8 (2000).

(56) References Cited

OTHER PUBLICATIONS

Edwards, "Thalidomide: Is there a silver lining?" *Science News* 131:198 (1987).

Elliot et al., "The proteasome: A new target for novel drug therapies," *Am. J. Clin. Pathol.* 116:637-646 (2001).

Figg et al., "Pharmacokinetics of thalidomide in an elderly prostate cancer population," *J. Pharm. Sci.* 88:121-125 (1999).

Filella et al., "Cytokines (IL-6, TNF-alpha, IL-1 alpha) and soluble interleukin-2 receptor as serum tumor markers in multiple myeloma," *Cancer Detect. Prev.* 20:52-56 (1996).

Foerster et al., "Effects of thalidomide and EM12 on the synthesis of TNF-α in coclutures of human.monocytes and lymphocytes," Abstract 517 (1995).

Gahrton et al., "Progress in haematopoietic stem cell transplantation for multiple myeloma," *J. Intern. Med.* 248:185-201 (2000).

Gardner et al., "Assessing the effectiveness of a computerized pharmacy system." In *Decision Support Systems in Critical Care*; Shabot et al., eds.; pp. 174-183 (1994).

Gennaro et al., Remington's Pharmaceutical Sciences, 17$^{th}$ edition, Mack Printing Company, Easton, PA, pp. 1613-1625 (1985).55791.

Glasmacher et al., "Oral idarubicin, dexamethasone and vincristine (VID) in the treatment of multiple myeloma," *Leukemia* 11:S22-S26 (1997).

Grönroos et al., "A medication database—a tool for detecting drug interactions in hospital," *Eur. J. Clin. Pharmacol.* 53:13-17 (1997).

Gupta et al., "Adherence of multiple myeloma cells to bone marrow stromal cells upregulates vascular endothelial growth factor secretion: therapeutic applications," *Leukemia*, 15(12):1950-1961 (2001).

Hamera et al., "Alcohol, cannabis, nicotine, and caffeine use and symptom distress in Schizophrenia," *J. Nerv. Ment. Dis.* 183:559-565 (1995).

He et al., "Synthesis of thalidomide analogs and their biological potential for treatment of graft versus host disease," 206th ACS National Meeting 0-8412-2620-2, American Chemical Society, Chicago, IL, Abstract 216 (1993).

Heger et al., "Embryotoxic effects of thalidomide derivatives in the non-human primate callithrixjacchus IV teratogenicity of µg/kg doses of the EMJ 2 enantiomers," *Teratog. Carcinog. Mutagen.* 14:115-122 (1994).

Hideshima et al., "Novel therapies targeting the myeloma cell and its bone marrow microenvironment," *Semin. Oncol.* 28:607-612 (2001).

Hideshima et al., "The proteasome inhibitor PS-341 inhibits growth, induces apoptosis, and overcomes drug resistance in human multiple myeloma cells," *Cancer Res.* 61:3071-3076 (2001).

Hideshima et al., "Thalidomide (Thal) and its analogs overcome drug resistance of human multiple myeloma (MM) cells to conventional therapy," *Abstract 1313, American Society of Hematology*, Dec. 1-5, 2000.

Hideshima et al., "Thalidomide and its analogs overcome drug resistance of human multiple myeloma cells to conventional therapy," *Blood* 96(9):2943-2950 (2000).

Hochster et al., "Activity and pharmacodynamics of 21-Day topotecan infusion in patients with ovarian cancer previously treated with platinum-based chemotherapy. New York Gynecologic Oncology Group," *J. Clin. Oncol.* 17:2553-2561 (1999).

Hus et al., "Thalidomide treatment of resistant or relapsed multiple myeloma patients," *Haematologica* 86:404-408 (2001).

Jagannath et al., "Pomalidomide (POM) with or without low-dose dexamethasone (LoDEX) in patients (Pts) with relapsed and refractory multiple myeloma (RRMM): MM-002 phase II age subgroup analysis," *J. Clin. Oncol.* 31, Abstrct # 8532, (2013).

Jönsson, "Chemical structure and teratogenic properties. 3. A review of available data on structure-activity relationships and mechanism of action of thalidomide analogues," *Acta Pharm. Suec.* 9:521-542 (1972).

Jourdan et al., "Tumor necrosis factor is a survival and proliferation factor for human myeloma cells," *Eur. Cytokine Netw.* 10:65-70 (1999).

Keravich et al., "Challenges of thalidomide distribution in a hospital setting," *Am. J. Health Syst. Pharm.* 56:1721-1725 (1999).

Kibbe ed., Handbook of Pharmaceutical Excipients, 3rd edition, pp. 160-162 (2000).

Kibbe, "Handbook of Pharmaceutical Excipients," Third Edition, extracts for lactose, mannitol and starch, pp. 276-285, 324-328 and 522-530 (2005).

Knight, "Cancer patients ahead of FDA on thalidomide use," *Washington Post* Jun. 25, 2001.

Kosten et al., "Substance abuse and Schizophrenia: Editors' Introduction," *Schizophrenia Bulletin* 23:181-186 (1997).

Kyle et al., "Therapeutic application of thalidomide in multiple myeloma," *Semin. Oncol.* 28:583-587 (2001).

Lacy et al., "Pomalidomide (CC4047) plus low-dose dexamethasone as therapy for relapsed multiple myeloma," *J. Clin. Oncol.* 27:5008-5014 (2009).

Lacy et al., "Pomalidomide plus low-dose dexamethasone in myeloma refractory to both bortezomib and lenalidomide: Comparison of 2 dosing strategies in dual-refractory disease," *Blood* 118:2970-2975 (2011).

Lee et al., "A pilot trial of hyperfractionated thoracic radiation therapy with concurrent cisplatin and oral etoposide for locally advanced inoperable non-small-cell lung cancer: a 5-year follow-up report," *Int. J Radiat. Oncol. Biol. Phys.* 42:479-486 (1998).

Lentzsch et al., "Immunomodulatory derivatives (IMiDs) of thalidomide (Thal) inhibit the proliferation of multiple myeloma (MM) cell lines and block VEGF-induced activation of the MAPK-pathway," *Blood* 96:579 (Abstract# 2486) (2000).

Lentzsch et al., "S-3-amino-phthalimido-glutarimide inhibits angiogenesis and growth of B-cell neoplasias in mice", *Cancer Research* 62:2300-2305 (2002).

Linnarsson, "Decision support for drug prescription integrated with computer-based patient records in primary care," *Med. Inform.* 18:131-142 (1993).

Lipkin, "Deriving new drugs from thalidomide," *Science News* 148:171 (1995).

Mann et al., "Passage of chemicals into human and animal semen: mechanisms and significance," *Crit. Rev. Toxicol.* 11:1-14 (1982).

Marriott et al., "Immunotherapeutic and antitumour potential of thalidomide analogues," *Expert Opin. Biol. Ther.* 1:1-8 (2001).

Marwick, "Thalidomide back—under strict control," *JAMA* 278:1135-1137 (1997).

Menill, "Substance Abuse and Women on Welfare," in *National Center on Addiction and Substance Abuse at Columbia University*, Jun. 1994.

Mitchell et al., "A pregnancy-prevention program in women of childbearing age receiving isotretinoin," *N. Engl. J. Med.* 333:101-106 (1995).

Mitsiades et al., "Concepts in the use of TRAIL/Apo2L: An emerging biotherapy for myeloma and other neoplasias," *Expert Opin. Investig. Drugs* 10:1521-1530 (2001).

Mitsiades et al., "Apoptic signaling induced by immunomodulatory thalidomide analogs in human multiple myeloma cells: therapeutic implications," *Blood*, 2002, 99:4525-4530, *American Society of Hematology*.

Montero et al., "Economic study of neutropenia induced by myelotoxic chemotherapy," *Pharm. World Sci.* 16:187-192 (1994).

Morgan et al., "Lenalidomide (Revlimid), in combination with cyclophosphamide and dexamethasone (RCD), is an effective and tolerated regimen for myeloma patients," *Br. J. Haematol.* 137:268-269 (2007).

Muller et al., "Amino-substituted thalidomide analogs: potent inhibitors of TNF-60 production," *Bioorg. Med. Chem. Lett.*, 9(11):1625-1630 (1999).

Muller, Thalidomide: From tragedy to new drug discovery, *Chemtech* 27:21-25 (1997).

Mundt, "Interactive voice response systems in clinical research and treatment," *Psychiatr. Serv.* 48:611-612, 623 (1997).

National Cancer Institute, Common Toxicity Criteria Manual, Ver. 2.0, Jun. 1, 1999.

(56) References Cited

OTHER PUBLICATIONS

NCT00480363: "QUIREDEX: Revlimid (lenalidomide) and dexamethasone (ReDex) treatment versus observation in patients with smoldering multiple myeloma with high risk of progression (QUIREDEX)," (2013).
Noguelra et al., "Effect of thalidomide and some derivatives on the adhesion of lymphocytes to endothelial cells," Abstract 518 (1995).
Notice of Opposition by Generics Limited, against EP Patent No. 2391355 mailed on Oct. 17, 2017.
Notice of Opposition by HGF Limited, against EP Patent No. 2391355 mailed on Oct. 17, 2017.
Notice of Opposition by Hoffmann Eitle against EP Patent No. 2391355 mailed on Oct. 18, 2017.
Notice of Opposition by STADA Arzneimittel AG, against EP Patent No. 2391355 mailed on Oct. 18, 2017.
Notice of Opposition by Teva Pharmaceutical Industries Ltd., against EP Patent No. 2391355 mailed on Oct. 12, 2017.
Olson et al., "Thalidomide (N-phthaloylglutamimide) in the treatment of advanced cancer," *Clin. Pharm. Ther.*, 6(3):292-297 (1965).
Palumbo et al., "Low-dose thalidomide plus dexamethasone is an effective salvage therapy for advanced myeloma," *Haematologica* 86:399-403 (2001).
Pastuszak et al., "Use of the retinoid pregnancy prevention program in Canada: Patterns of contraception use in women treated with isotretinoin and etretinate," *Reprod. Toxicol.* 8:63-68 (1994).
Patentee's Response to the Communication pursuant to Article 94(3) EPC in EP Patent No. 2391355 dated Mar. 24, 2015.
Pestotnik et al., "Therapeutic antibiotic monitoring: Surveillance using a computerized expert system," *Am. J. Med.* 88:43-48 (1990).
Piper et al., "Anti-inflammatory immunosuppressive thalidomide analogs. Screening," *Int. J Leprosy* 49:511-512 (1981).
Powell et al., "Guideline for the clinical use and dispensing of thalidomide," *Postgrad. Med. J.* 70:901-904 (1994).
Pro et al., "Phase II study of thalidomide in patients with recurrent Hodgkin's disease (HD) and non-Hodgkin's lymphoma (NHL)," *Blood* 98:246b (Abstract# 4712) (2001).
Querfeld et al., "Preliminary results of a phase II study of CC-5013 (lenalidomide, revlimid®) in patients with cutaneous T-cell lymphoma," *Blood* 106:936a-937a (2005).
Raje et al., "Thalidomide—a revival story," *N. Engl. J. Med.* 341(21):1606-1609 (1999).
Rajkumar et al., "Lenalidomide plus high-dose dexamethasone versus lenalidomide plus low-dose dexamethasone as initial therapy for newly diagnosed multiple myeloma: an open-label randomised controlled trial," *Lancet* 11:29-37 (2010).
Rajkumar et al., "Phase III trial of lenalidomide plus highdose dexamethasone versus lenalidomide plus low-dose dexamethasone in newly diagnosed multiple myeloma (E4A03): A trial coordinated by the Eastern Cooperative Oncology Group," *J. Clin. Oncol.* 25:18S (2007).
Rajkumar et al., "Thalidomide plus dexamethasone (Thal/Dex) and thalidomide alone (Thal) as first line therapy for newly diagnosed myeloma (MM)," *Blood* 96(Supp.):168a (2000).
Rajkumar et al., "Combination therapy with lenalidomide plus dexamethasone (Rev/Dex) for newly diagnosed myeloma," *Blood*, 106(13):4050-4053 (2005).
Rajkumar et al., "Thalidomide in the treatment of plasma cell malignancies," *J. Clin. Oncol.* 19:3593-3595 (2001).
Rajkumar, "Thalidomide in multiplem myeloma," *Oncology* 14:11-16 (2000).
Ratain, "Pharmacology of Cancer Chemotherapy." In *Cancer: Principles & Practice of Oncology*, pp. 335-459 (2001).
Reiman et al., "Meeting synopsis, VIII International Myeloma Workshop, Banff Springs Hotel, Banff, Alberta, Canada, May 4-8, 2001," *Eur. J. Haematol.* 67:199-202 (2001).
Reist et al., "Chiral inversion and hydrolysis of thalidomide: mechanisms and catalysis by bases and serum albumin, and chiral stability of teratogenic metabolites," *Chem. Res. Toxicol.*, 11:1521-1528 (1998).

Ribatti et al., "Angiogenesis spectrum in the stroma of B-cell non-Hodgkin's lymphomas. An immunohistochemical and ultrastructural study," *Eur. J. Haematol.* 56:45-53 (1996).
Richardson et al., "A randomized phase 2 study of lenalidomide therapy for patients with relapsed or relapsed and refractory multiple myeloma," *Blood* 108:3458-3464 (2006).
Richardson et al., "Thalidomide in multiple Myeloma," *Biomed. Pharmacother.* 56:115-128 (2002).
Richardson et al., "Thalidomide: Emerging role in cancer medicine," *Ann. Rev. Med.* 53:629-657 (2002).
Richardson et al., "A phase 1 study of oral CC5013, an immunomodulatory thalidomide (Thal) derivative, in patients with relapsed and refractory multiple myeloma (MM)," *Blood* 98:775a (2001).
Richardson et al., "A phase 1/2 multi-center, randomized, open label dose escalation study to determine the maximum tolerated dose (MTD), safety, and efficacy of pomalidomide (POM) alone or in combination with low-dose dexamethasone (DEX) in patients (PTS) with relapsed and refractory multiple myeloma (RRMM) who have received prior treatment (TX) that includes lenalidomide (LEN) and bortezomib (BORT)," *Haematologica*, 96:S31 (2011).
Richardson et al., "A Phase I study of oral CC5013, an immunomodulatory thalidomide (Thal) derivative, in patients with relapsed and refractory multiple myeloma (MM)," *Blood*, 98(11), Abstract# 3225 (2001).
Richardson et al., "A phase I study of the safety and efficacy of CC5013 treatment for patients with relapsed multiple myeloma: Preliminary results," VIII the International Myeloma Workshop, Banff, Alberta, Canada, May 4-8, 2001; Abstract #P230.
Richardson et al., "Immunomodulatory drug CC-5013 overcomes drug resistance and is well tolerated in patients with relapsed multiple myeloma," Blood 100:3063-3067 (2002).
Robert et al., "Phase I and pharmacologic study of 7- and 21-day continuous etoposide infusion in patients with advanced cancer," *Cancer Chemother. Pharmacol.* 38:459-465 (1996).
Rowe et al., "Handbook of Pharmaceutical Excipients," 6$^{th}$ edition, pp. 424-428 and 685-691 (2009).
Samlowski et al., "Evaluation of gemcitabine in patients with recurrent or metastatic squamous cell carcinoma of the head and neck: A southwest oncology group phase II study," *Invest. New Drugs* 19:311-315 (2001).
Sampaio et al., "Prolonged treatment with recombinant interferon gamma induces erythema nodosum leprosum in lepromatous leprosy patients," *J. Exp. Med.* 175:1729-1737 (1992).
Sampaio et al., "Thalidomide selectively inhibits tumor necrosis factor alpha production by stimulated human monocytes," *J. Exp. Med.* 173:699-703 (1991).
Schey et al., "Phase I Study of an Immunomodulatory Thalidomide Analog, CC-4047, in Relapsed or Refractory Multiple Myeloma," *J. Clin. Oncol.* 22(16):3269-3276 (2004).
Schey et al., "Pomalidomide therapy for myeloma," *Expert Opin. Invest. Drugs* 20:691-700 (2011).
Schey et al., "A phase I study of an immunomodulatory thalidomide analogue (CC4047) in relapse/refractory multiple myeloma," *International Society for Experimental Hematology*, Abstract #248, (2002).
Schey, "Thalidomide in the management of multiple myeloma," *Hematology* 7:291-299 (2002).
Schlossman et al., "Bone marrow transplatation in multiple myeloma," *Curr. Opin. Oncol.* 11:102-108 (1999).
Seppa, "Thalidomide combats myeloma blood cancer," *Science News* 156:326 (1999).
Shinn et al., "Development of a computerized drug interaction database (MEDICOM) for use in a patient specific environment," *Drug Inf. J.* 17 :205-210 (1983).
Siegel et al., "Long-term safety and efficacy of pomalidomide (POM) with or without low-dose dexamethasone (LoDEX) in relapsed and refractory multiple myeloma (RRMM) patients enrolled in the MM-002 phase II trial," *J. Clin. Oncol.* 31, 2013 (Abstract No. 8588).
Singhal et al., "Antitumor activity of thalidomide in refractory multiple myeloma," *N. Engl. J. Med.*, 341(21):1565-1571 (1999).
Smith, R. et al.,"Studies on the Relationship Between the Chemical Structure and Embryotoxic Activity of Thalidomide and Related

(56) References Cited

OTHER PUBLICATIONS

Compounds," in *A Symposium on Embryopathic Activity of Drugs*, J. & A. Churchill Ltd., Session 6, pp. 194-209 (1965).
Sorbera et al., "CC-5013. Treatment of multiple myeloma. Treatment of Melanoma. Treatment of myelodysplastic syndrome. Angiogenesis inhibitor. TNF-α production inhibitor," *Drugs of the Future*, 28(5):425-431 (2003).
Soyka et al., "Prevalence of alcohol and drug abuse in schizophrenic inpatients," *Eur. Arch. Psychiatry Clin. Neurosci.* 242:362-372 (1993).
Srkalovic et al. "Use of melphalan, thalidomide, and dexamethasone in treatment of refractory and relapsed multiple myeloma," *Med. Oncol.* 19:219-226 (2002).
Steiner et al., "The assessment of refill compliance using pharmacy records: methods, validity, and applications," *J. Clin. Epidemiol.* 50:105-116 (1997).
Stirling et al., "Thalidomide. A surprising recovery," *J. Am. Pharm. Assoc.* N537:306-313 (1997).
Stirling, "Thalidomide: A novel template for anticancer drugs," *Seminars Oncology* 28:602-606 (2001).
Szelényi et al., "Cyclophosphamide, adriamycin and dexamethasone (CAD) is a highly effective therapy for patients with advanced multiple myeloma," *Ann. Oncol.* 12:105-108 (2001).
THALOMID® (thalidomide) Capsules (50, 100, 200 mg) Label, FDA, (2006).
THALOMID™ (thalidomide) Capsules Revised Package Insert (Jul. 15, 1998).
The Comprehensive Guide to Banff, Understanding the VIIIth International Myeloma Workshop published by the International Myeloma Foundation (2001).
Thomas et al., "Current role of thalidomide in cancer treatment," *Curr. Opin. Oncol.* 12:564-573 (2000).
Transcript of the Forty-Seventh Meeting of the Dermatologic and Ophthalmic Drugs Advisory Committee (Sep. 4, 1997).
Transcript of the Forty-Seventh Meeting of the Dermatologic and Ophthalmic Drugs Advisory Committee (Sep. 5, 1997).
Tseng et al., "Rediscovering thalidomide: a review of its mechanism of action, side effects, and potential uses," *J. Am. Acad. Dermatol.* 35:969-979 (1996).
Udagawa et al., "Thalidomide and analogs," in Antiangiogenic Agents in Cancer Therapy, B. Teicher (ed.), Human Press Inc., Totowa, NJ, Chapter 16, pp. 263-274 (1998).
Vacca et al., "Angiogenesis in B cell lymphoproliferative diseases. Biological and clinical studies," *Leuk. Lymphoma* 20:27-38 (1995).
Vij et al., "Pomalidomie (POM) with Low-Dose Dexamethasone (LoDex) in Patients with Relapsed and Refractory Multiple Myeloma (RRMM): Outcomes Based on Prior Treatment Exposure," presented at 54th ASH Annual Meeting and Exposition, Atlanta, Georgia, Dec. 8-11, 2012, Abstract #4070.
Vippagunta et al., "Crystalline solids," *Adv. Drug Deliv. Rev.*, 48(1):3-26 (2001).
Vogelsang et al., "Thalidomide for the treatment of chronic graft-versus-host disease," *N. Engl. J. Med.* 326:1055-1058 (1992).
Weber et al., "Thalidomide alone or with dexamethasone for multiple myeloma," *Blood* 94:604 (1999).
Weber et al., "Thalidomide with dexamethasone for resistant multiple myeloma," *Blood* 96:167 (2000).
Welte et al., "Influence of socially desirable responding in a study of stress and substance abuse," *Alcohol Clin. Exp. Res.* 17:758-761 (1993).
Wilson et al., "Response to thalidomide in chemotherapy-resistant mantle cell lymphoma: a case report," *Br. J. Haematol.* 119:128-130 (2002).
Yuen et al., "Phase I study of an antisense oligonucleotide to protein kinase C-α (ISIS 3521/CGP 64128A) in patients with cancer," *Clin. Cancer Res.* 5:3357-3363 (1999).

Zangari et al., "Increased risk of deep-vein thrombosis in patients with multiple myeloma receiving thalidomide chemotherapy," *Blood* 98:1614 (2001).
Zangari et al., Results of phase I study of CC-5013 for the treatment of multiple myeloma (MM) patients who relapse after high dose chemotherapy (HDT), *Blood* 98(11), Abstract# 3226 (2001).
Zangari et al., "Thrombogenic activity of doxorubicin in myeloma patients receiving thalidomide: implications for therapy," *Blood*, 100:1168-1171 (2002).
Zeldis et al., "S.T.E.P.S.: A comprehensive program for controlling and monitoring access to thalidomide," *Clin. Ther.* 21:319-330 (1999).
Rudnic & Schwartz, "Oral solid dosage forms," *Remington's: The Science and Practice of Pharmacy*, $20^{th}$ edition, A. Gennaro (ed.), Lippincott Williams & Wildins, Baltimore, MD, pp. 858, 886 (2000).
Rowe et al., "Handbook of Pharmaceutical Excipients," $4^{th}$ edition, pp. 373-377 (2003).
Aulton ed., *Aulton's Pharmaceutics: The Design and Manufacture of Medicines*, $3^{rd}$ Edition, Churchill Livingstone, London, UK, pp. 336-360, 441-482, 515-538 (2007).
Banker & Rhodes, *Modern Pharmaceutics*, $4^{th}$ Ed., Marcel Dekker, Inc., New York, New York, pp. 172-174 (2002).
Chang et al., "Roller compaction, granulation and capsule product dissolution of drug formulations containing a lactose or mannitol filler, starch, and talc," *AAPS PharmSciTech*, 9(2):597-604 (2008).
Jones ed., *Pharmaceutics—Dosage Form and Design*, Pharmaceutical Press, London, UK, pp. 203-271 (2008).
Jones, "The filling of powders into two-piece hard capsules," *Int. i Pharm.*, 227(1-2):5-26 (2001).
Jones, "Two-piece gelatin capsules: excipients for powder products, European practice," *Pharm. Tech. Europe*, 7(10):25-34 (1995).
Lau, "5-Preformulation Studies," *Handbook of Modern Pharmaceutical Analysis*, vol. 3, pp. 173-233 (2001).
Marriott et al., "Thalidomide and its analogues have distinct and opposing effects on TNF-α and TNFR2 during co-stimulation of both CD4+ and CD8+ T cells," *Clin. Exp. Immunol.*, 130:75-84 (2002).
Nabors ed., Alternative Sweeteners, $3^{rd}$ Edition, Marcel Dekker, Inc., Basel, CH, pp. 317-334 (2001).
Pifferi et al., "Quality and fuctionality of excipients," *II Farmaco*, 54(1-2):1-14 (1999).
Rasenack et al., "Crystal habit and tableting behavior," *Int. i Pharm.* 244(1-2):45-57 (2002).
*Remington's Pharmacautical Sciences*, Mack Publishing, Easton, PA, pp. 1603-1632 (1985).
Richardson et al., "Immunomodulatory analogs of thalidomide: an emerging new therapy in myeloma," *J. Clin. Oncol.*, 22(16):3212-3214 (2004).
Rowe et al. ed., *Handbook of Pharmaceutical Excipients*, $5^{th}$ Edition, Pharmaceutical Press, London, UK, pp. 93-101 (2006).
Rowe et al. ed., *Handbook of Pharmaceutical Excipients*, $5^{th}$ Edition, Pharmaceutical Press, London, UK, pp. 132-135 (2006).
Rowe et al. ed., *Handbook of Pharmaceutical Excipients*, $5^{th}$ Edition, Pharmaceutical Press, London, UK, pp. 449-453, 705-707, 725-733, and Appendix I (2006).
Sison et al., "Phase II study of CC-4047 in patients with metastatic hormone-refractory prostate cancer (HRPCa)," *J. Clin. Oncol.*, 22(14):4701 (2004).
*Starch 1500 Partially Pregelatinized Maize Starch*, Colorcon, West Point, PA, 6 pages (1999).
Streetly et al., "Alternate Day Actimid™ (CC-4047) is well tolerated and is active when used to treat relapsed/refractory myeloma," *Blood*, 104:332 (2004).
Yoshinari et al., "Moisture induced polymorphic transition of mannitol and its morphological transformation," *Int. J. Pharm.*, 247(1-2):69-77 (2002).

\* cited by examiner

FORMULATIONS OF 4-AMINO-2-(2,6-DIOXOPIPERIDINE-3-YL)ISOINDOLINE-1,3-DIONE

This application is a continuation of co-pending U.S. patent application Ser. No. 14/998,262, filed Dec. 23, 2015, which is a continuation of U.S. patent application Ser. No. 14/447,450, filed Jul. 30, 2014, which is a continuation of U.S. patent application Ser. No. 12/783,390, filed May 19, 2010, now U.S. Pat. No. 8,828,427, which claims priority to U.S. Provisional Application No. 61/179,678, filed May 19, 2009, each of which are incorporated herein by reference in their entireties.

1. FIELD

Provided herein are formulations and dosage forms of pomolidomide, i.e., 4-amino-2-(2,6-dioxopiperidine-3-yl)isoindoline-1,3-dione or CC-4047. Methods of using the formulations and dosage forms are also provided herein.

2. BACKGROUND

Drug substances are usually administered as part of a formulation in combination with one or more other agents that serve varied and specialized pharmaceutical functions. Dosage forms of various types may be made through selective use of pharmaceutical excipients. As pharmaceutical excipients have various functions and contribute to the pharmaceutical formulations in many different ways, e.g., solubilization, dilution, thickening, stabilization, preservation, coloring, flavoring, etc. The properties that are commonly considered when formulating an active drug substance include bioavailability, ease of manufacture, ease of administration, and stability of the dosage form. Due to the varying properties of the active drug substance to be formulated, dosage forms typically require pharmaceutical excipients that are uniquely tailored to the active drug substance in order to achieve advantageous physical and pharmaceutical properties.

Pomolidomide, which is also known as CC-4047, is chemically named 4-amino-2-(2,6-dioxopiperidine-3-yl)isoindoline-1,3-dione. Pomolidomide is an immunomodulatory compound that inhibits, for example, LPS induced monocyte TNFα, IL-1β, IL-12, IL-6, MIP-1, MCP-1, GM-CSF, G-CSF, and COX-2 production. The compound is also known to co-stimulate the activation of T-cells. Pomolidomide and method of synthesizing the compound are described, e.g., in U.S. Pat. No. 5,635,517, the entirety of which is incorporated herein by reference.

Due to its diversified pharmacological properties, pomolidomide is useful in treating, preventing, and/or managing various diseases or disorders. Thus, a need exists as to dosage forms of pomolidomide having advantageous physical and pharmaceutical properties.

3. SUMMARY

Provided herein are pharmaceutical dosage forms of pomolidomide, or a pharmaceutically acceptable stereoisomer, prodrug, salt, solvate, hydrate, or clathrate thereof. Also provided herein are methods of treating, managing, or preventing diseases and conditions such as, but not limited to, cancer, pain, Macular Degeneration, a skin disease, a pulmonary disorder, an asbestos-related disorder, a parasitic disease, an immunodeficiency disorder, a CNS disorder, CNS injury, atherosclerosis, a sleep disorder, hemoglobinopathy, anemia, an inflammatory disease, an autoimmune disease, a viral disease, a genetic disease, an allergic disease, a bacterial disease, an ocular neovascular disease, a choroidal neovascular disease, a retina neovascular disease, and rubeosis, using pomolidomide, or a pharmaceutically acceptable stereoisomer, prodrug, salt, solvate, hydrate, or clathrate thereof, in the dosage forms described herein.

3.1. Definitions

As used herein and unless otherwise indicated, a composition that is "substantially free" of a compound means that the composition contains less than about 20 percent by weight, more preferably less than about 10 percent by weight, even more preferably less than about 5 percent by weight, and most preferably less than about 3 percent by weight of the compound.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80 percent by weight of one stereoisomer of the compound and less than about 20 percent by weight of other stereoisomers of the compound, more preferably greater than about 90 percent by weight of one stereoisomer of the compound and less than about 10 percent by weight of the other stereoisomers of the compound, even more preferably greater than about 95 percent by weight of one stereoisomer of the compound and less than about 5 percent by weight of the other stereoisomers of the compound, and most preferably greater than about 97 percent by weight of one stereoisomer of the compound and less than about 3 percent by weight of the other stereoisomers of the compound.

As used herein and unless otherwise indicated, the term "enantiomerically pure" means a stereomerically pure composition of a compound having one chiral center.

As used herein, unless otherwise specified, the term "pharmaceutically acceptable salt(s)," as used herein includes, but is not limited to, salts of acidic or basic moieties of thalidomide. Basic moieties are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (i.e., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein, and unless otherwise specified, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of thalidomide that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of thalidomide that include —NO, —NO$_2$, —ONO, or —ONO$_2$ moieties.

As used herein and unless otherwise indicated, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, and unless otherwise specified, the terms "treat," "treating" and "treatment" contemplate an action that occurs while a patient is suffering from the specified disease or disorder, which reduces the severity of the disease or disorder, or retards or slows the progression of the disease or disorder.

As used herein, and unless otherwise specified, the terms "prevent," "preventing" and "prevention" refer to the prevention of the onset, recurrence or spread of a disease or disorder, or of one or more symptoms thereof. The terms "prevent," "preventing" and "prevention" contemplate an action that occurs before a patient begins to suffer from the specified disease or disorder, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 30%, 25%, 20%, 15%, 10%, or 5% of the specified dose, amount, or weight percent is encompassed.

As used herein, and unless otherwise specified, the term "stable," when used in connection with a formulation or a dosage form, means that the active ingredient of the formulation or dosage form remains solubilized for a specified amount of time and does not significantly degrade or aggregate or become otherwise modified (e.g., as determined, for example, by HPLC). In some embodiments, about 70 percent or greater, about 80 percent or greater or about 90 percent or greater of the compound remains solubilized after the specified period.

4. DETAILED DESCRIPTION

Provided herein are pharmaceutical dosage forms of pomolidomide, or a pharmaceutically acceptable stereoisomer, prodrug, salt, solvate, hydrate, or clathrate thereof. In some embodiments, the dosage forms are suitable for oral administration to a patient. In other embodiments, the dosage forms provided herein exhibit advantageous physical and/or pharmacological properties. Such properties include, but are not limited to, ease of assay, content uniformity, flow properties for manufacture, dissolution and bioavailability, and stability. In certain embodiments, the dosage forms provided herein have a shelf life of at least about 12 months, at least about 24 months, or at least about 36 months without refrigeration.

Also provided herein are kits comprising pharmaceutical compositions and dosage forms provided herein. Also provided herein are methods of treating, managing, and/or preventing a disease or condition, which comprises administering to a patient in need thereof a pharmaceutical composition or a dosage form provided herein.

4.1 Compositions and Dosage Forms

In one embodiment, provided herein is a single unit dosage form suitable for oral administration to a human comprising: an amount equal to or greater than about 1, 5, 10, 15, 20, 25, 30, 50, 75, 100, 150, or 200 mg of an active ingredient; and a pharmaceutically acceptable excipient; wherein the active ingredient is pomolidomide, or a pharmaceutically acceptable stereoisomer, prodrug, salt, solvate, or clathrate thereof. In some embodiments, the amount of active ingredient is from about 0.1 to about 100 mg, from about 0.5 to about 50 mg, from, about 0.5 to about 25 mg, from about 1 mg to about 10 mg, from about 0.5 to about 5 mg, or from about 1 mg to about 5 mg. In one embodiment, the amount of the active ingredient is about 0.5 mg. In another embodiment, the amount of the active ingredient is about 1 mg. In another embodiment, the amount of the active ingredient is about 2 mg. In another embodiment, the amount of the active ingredient is about 5 mg.

Pharmaceutical compositions and formulations provided herein can be presented as discrete dosage forms, such as capsules (e.g., gelcaps), caplets, tablets, troches, lozenges, dispersions, and suppositories each containing a predetermined amount of an active ingredient as a powder or in granules, a solution, or a suspension in an aqueous or non-aqueous liquid, an oil-in-water emulsion, or a water-in-oil liquid emulsion. Because of their ease of administration, tablets, caplets, and capsules represent a preferred oral dosage unit forms.

Tablets, caplets, and capsules typically contain from about 50 mg to about 500 mg of the pharmaceutical composition (i.e., active ingredient and excipient(s)). Capsules can be of any size. Examples of standard sizes include #000, #00, #0, #1, #2, #3, #4, and #5. See, e.g., *Remington's Pharmaceutical Sciences*, page 1658-1659 (Alfonso Gennaro ed., Mack Publishing Company, Easton Pa., 18th ed., 1990), which is incorporated by reference. In some embodiments, capsules provided herein are of size #1 or larger, #2 or larger, or #4 or larger.

Also provided herein are anhydrous pharmaceutical compositions and dosage forms including an active ingredient, since water can facilitate the degradation of some compounds. For example, the addition of water (e.g., 5 percent) is widely accepted in the pharmaceutical arts as a means of simulating shelf-life, i.e., long-term storage in order to determine characteristics such as shelf-life or the stability of formulations over time. See, e.g., Jens T. Carstensen, *Drug Stability: Principles & Practice*, 2d. Ed., Marcel Dekker, N.Y., NY, 1995, pp. 379-80. In effect, water and heat accelerate decomposition. Thus, the effect of water on a formulation can be of great significance since moisture and/or humidity are commonly encountered during manufacture, handling, packaging, storage, shipment, and use of formulations.

An anhydrous pharmaceutical compositions should be prepared and stored such that the anhydrous nature is maintained. Accordingly, in some embodiments, anhydrous compositions are packaged using materials known to prevent exposure to water such that they can be included in suitable formulary kits. Examples of suitable packaging include, but are not limited to, hermetically sealed foils, plastic or the like, unit dose containers, blister packs, and strip packs.

In this regard, also provided herein is a method of preparing a solid pharmaceutical formulation including an active ingredient through admixing the active ingredient and an excipient under anhydrous or low moisture/humidity conditions, wherein the ingredients are substantially free of water. The method can further include packaging the anhydrous or non-hygroscopic solid formulation under low moisture conditions. By using such conditions, the risk of contact with water is reduced and the degradation of the active ingredient can be prevented or substantially reduced.

Also provided herein are lactose-free pharmaceutical compositions and dosage forms. Compositions and dosage forms that comprise an active ingredient that is a primary or secondary amine are preferably lactose-free. As used herein, the term "lactose-free" means that the amount of lactose present, if any, is insufficient to substantially increase the degradation rate of an active ingredient that is a primary or secondary amine. Lactose-free compositions provided herein can comprise excipients which are well known in the art and are listed in the USP (XXI)/NF (XVI), which is incorporated herein by reference.

In one embodiment, pomolidomide, or a pharmaceutically acceptable stereoisomer, prodrug, salt, solvate, or clathrate thereof, comprises from about 0.1 to about 10 weight percent of total weight of the composition. In another embodiment, pomolidomide, or a pharmaceutically acceptable stereoisomer, prodrug, salt, solvate, or clathrate thereof, comprises from about 0.1 to about 5 weight percent of total weight of the composition. In another embodiment, pomolidomide, or a pharmaceutically acceptable stereoisomer, prodrug, salt, solvate, or clathrate thereof, comprises from about 0.1 to about 3 weight percent of total weight of the composition. In another embodiment, pomolidomide, or a pharmaceutically acceptable stereoisomer, prodrug, salt, solvate, or clathrate thereof, comprises from about 0.5 to about 3 weight percent of total weight of the composition. In another embodiment, pomolidomide, or a pharmaceutically acceptable stereoisomer, prodrug, salt, solvate, or clathrate thereof, comprises from about 0.5 to about 2 weight percent of total weight of the composition. In another embodiment, pomolidomide, or a pharmaceutically acceptable stereoisomer, prodrug, salt, solvate, or clathrate thereof, comprises about 1 weight percent of total weight of the composition. In another embodiment, pomolidomide, or a pharmaceutically acceptable stereoisomer, prodrug, salt, solvate, or clathrate thereof, comprises about 0.8 weight percent of total weight of the composition. In another embodiment, pomolidomide, or a pharmaceutically acceptable stereoisomer, prodrug, salt, solvate, or clathrate thereof, comprises about 2 weight percent of total weight of the composition. In another embodiment, pomolidomide, or a pharmaceutically acceptable stereoisomer, prodrug, salt, solvate, or clathrate thereof, comprises about 1.7 weight percent of total weight of the composition.

In one embodiment, the active ingredient and carrier, diluent, binder, or filler are directly blended as described herein elsewhere. In another embodiment, the carrier, diluent, binder, or filler comprises mannitol and/or starch. In one embodiment, the mannitol is spray dried mannitol. In another embodiment, the starch is pregelatinized starch.

In one embodiment, the carrier, diluent, binder, or filler comprises from about 70 to about 99 weight percent of total weight of the composition. In another embodiment, the carrier, diluent, binder, or filler comprises from about 80 to about 99 weight percent of total weight of the composition. In another embodiment, the carrier, diluent, binder, or filler comprises from about 85 to about 99 weight percent of total weight of the composition. In another embodiment, the carrier, diluent, binder, or filler comprises from about 90 to about 99 weight percent of total weight of the composition. In another embodiment, the carrier, diluent, binder, or filler comprises from about 95 to about 99 weight percent of total weight of the composition. In another embodiment, the carrier, diluent, binder, or filler comprises about 98 weight percent of total weight of the composition. In another embodiment, the carrier, diluent, binder, or filler comprises about 99 weight percent of total weight of the composition.

In one embodiment, the dosage forms provided herein comprise both mannitol and starch. In one embodiment, mannitol and starch comprise from about 70 to about 99 weight percent of total weight of the composition. In another embodiment, mannitol and starch comprise from about 80 to about 99 weight percent of total weight of the composition.

In another embodiment, mannitol and starch comprise from about 85 to about 99 weight percent of total weight of the composition. In another embodiment, mannitol and starch comprise from about 90 to about 99 weight percent of total weight of the composition. In another embodiment, mannitol and starch comprise from about 95 to about 99 weight percent of total weight of the composition. In another embodiment, mannitol and starch comprise about 98 weight percent of total weight of the composition. In another embodiment, mannitol and starch comprise about 99 weight percent of total weight of the composition.

In one embodiment, the ratio of mannitol:starch in the dosage form is from about 1:1 to about 1:1.5. In one embodiment, the ratio of mannitol:starch in the dosage form is about 1:1.3.

In another embodiment, the dosage form comprises a lubricant. In one embodiment, the dosage form comprises about 0.2, 0.3, 0.5, 0.6, or 0.8 mg of lubricant. In another embodiment, the dosage form comprises about 0.16, 0.32, 0.64, or 0.75 mg of lubricant. In one embodiment, the lubricant is sodium stearyl fumarate (PRUV).

In one embodiment, the lubricant, e.g., PRUV, comprises from about 0.01 to about 5 weight percent of total weight of the composition. In another embodiment, the lubricant, e.g., PRUV, comprises from about 0.01 to about 1 weight percent of total weight of the composition. In another embodiment, the lubricant, e.g., PRUV, comprises from about 0.1 to about 1 weight percent of total weight of the composition. In another embodiment, the lubricant, e.g., PRUV, comprises from about 0.1 to about 0.5 weight percent of total weight of the composition. In another embodiment, the lubricant, e.g., PRUV, comprises from about 0.2 to about 0.3 weight percent of total weight of the composition. In another embodiment, the lubricant, e.g., PRUV, comprises about 0.25 weight percent of total weight of the composition.

In some embodiments, because it is typical to obtain pomolidomide, or a pharmaceutically acceptable stereoisomer, prodrug, salt, solvate, or clathrate thereof, at a purity of less than 100%, the formulations and dosage forms provided herein may be defined as compositions, formulations, or dosage forms that comprise pomolidomide, or a pharmaceutically acceptable stereoisomer, prodrug, salt, solvate, or clathrate thereof, at an amount that provides the potency of a specified amount of 100% pure pomolidomide.

For example, in one embodiment, provided herein is a single unit dosage form comprising: 1) pomolidomide, or a pharmaceutically acceptable stereoisomer, prodrug, salt, solvate, or clathrate thereof, present at an amount that provides about 0.5, 1, 2, 3, 4, or 5 mg potency of pomolidomide; and 2) about 60, 120, 250, 180, 240, or 300 mg of a carrier, diluent, binder, or filler, respectively. In one embodiment, the amount of a carrier, diluent, binder, or filler is about 62, 124, 248, 177, 236, or 295 mg, respectively.

In one embodiment, provided herein is a dosage form comprising: 1) pomolidomide, or a pharmaceutically acceptable stereoisomer, prodrug, salt, solvate, or clathrate thereof, present at an amount that provides about 0.5 mg potency of pomolidomide; and 2) a pharmaceutically acceptable excipient. In one embodiment, the total weight of the dosage form is about 62.5 mg. In one embodiment, the dosage form is suitable for administration in a size 4 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 62.5 mg, the carrier, diluent, binder, or filler comprises mannitol and/or starch. In one embodiment, the excipient comprises both mannitol and starch. In one embodiment, where both mannitol and starch are present in the dosage form, the dosage form comprises about 35 mg of starch, and the remaining weight is filled by starch. In one embodiment, the mannitol is spray dried mannitol. In another embodiment, the starch is pregelatinized starch.

In one embodiment where the total weight of the dosage form is about 62.5 mg and where a lubricant is present, the lubricant is sodium stearyl fumarate. In one embodiment, the sodium stearyl fumarate is present at an amount of about 0.2 mg. In one embodiment, the sodium stearyl fumarate is present at an amount of about 0.16 mg.

In one embodiment, provided herein is a dosage form comprising: 1) pomolidomide, or a pharmaceutically acceptable stereoisomer, prodrug, salt, solvate, or clathrate thereof, present at an amount that provides about 0.5 mg potency of pomolidomide; 2) about 35 mg of pregelatinized starch; 3) about 0.16 mg of sodium stearyl fumarate; and 4) spray dried mannitol at an amount that brings the total weight of the dosage form to 62.5 mg. In one embodiment, the dosage form is suitable for administration in a size 4 or larger capsule.

In one embodiment, provided herein is a dosage form comprising: 1) pomolidomide, or a pharmaceutically acceptable stereoisomer, prodrug, salt, solvate, or clathrate thereof, present at an amount that provides about 1 mg potency of pomolidomide; and 2) a pharmaceutically acceptable excipient. In one embodiment, the total weight of the dosage form is about 125 mg. In one embodiment, the dosage form is suitable for administration in a size 4 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 125 mg, the carrier, diluent, binder, or filler comprises mannitol and/or starch. In one embodiment, the excipient comprises both mannitol and starch. In one embodiment, where both mannitol and starch are present in the dosage form, the dosage form comprises about 70 mg of starch, and the remaining weight is filled by starch. In one embodiment, the mannitol is spray dried mannitol. In another embodiment, the starch is pregelatinized starch.

In one embodiment where the total weight of the dosage form is about 125 mg and where a lubricant is present, the lubricant is sodium stearyl fumarate. In one embodiment, the sodium stearyl fumarate is present at an amount of about 0.3 mg. In one embodiment, the sodium stearyl fumarate is present at an amount of about 0.32 mg.

In one embodiment, provided herein is a dosage form comprising: 1) pomolidomide, or a pharmaceutically acceptable stereoisomer, prodrug, salt, solvate, or clathrate thereof, present at an amount that provides about 1 mg potency of pomolidomide; 2) about 70 mg of pregelatinized starch; 3) about 0.32 mg of sodium stearyl fumarate; and 4) spray dried mannitol at an amount that brings the total weight of the dosage form to 125 mg. In one embodiment, the dosage form is suitable for administration in a size 4 or larger capsule.

In one embodiment, provided herein is a dosage form comprising: 1) pomolidomide, or a pharmaceutically acceptable stereoisomer, prodrug, salt, solvate, or clathrate thereof, present at an amount that provides about 2 mg potency of pomolidomide; and 2) a pharmaceutically acceptable excipient. In one embodiment, the total weight of the dosage form is about 250 mg. In one embodiment, the dosage form is suitable for administration in a size 2 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 250 mg, the carrier, diluent, binder, or filler comprises mannitol and/or starch. In one embodiment, the excipient comprises both mannitol and starch. In one embodiment, where both mannitol and starch are present in the dosage form, the dosage form comprises about 140 mg of starch, and the remaining weight is filled by starch. In one embodiment, the mannitol is spray dried mannitol. In another embodiment, the starch is pregelatinized starch.

In one embodiment where the total weight of the dosage form is about 250 mg and where a lubricant is present, the lubricant is sodium stearyl fumarate. In one embodiment, the sodium stearyl fumarate is present at an amount of about 0.6 mg. In one embodiment, the sodium stearyl fumarate is present at an amount of about 0.64 mg.

In one embodiment, provided herein is a dosage form comprising: 1) pomolidomide, or a pharmaceutically acceptable stereoisomer, prodrug, salt, solvate, or clathrate thereof, present at an amount that provides about 2 mg potency of pomolidomide; 2) about 140 mg of pregelatinized starch; 3) about 0.64 mg of sodium stearyl fumarate; and 4) spray dried mannitol at an amount that brings the total weight of the dosage form to 250 mg. In one embodiment, the dosage form is suitable for administration in a size 2 or larger capsule.

In one embodiment, provided herein is a dosage form comprising: 1) pomolidomide, or a pharmaceutically acceptable stereoisomer, prodrug, salt, solvate, or clathrate thereof, present at an amount that provides about 3 mg potency of pomolidomide; and 2) a pharmaceutically acceptable excipient. In one embodiment, the total weight of the dosage form is about 180 mg. In one embodiment, the dosage form is suitable for administration in a size 2 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 180 mg, the carrier, diluent, binder, or filler comprises mannitol and/or starch. In one embodiment, the excipient comprises both mannitol and starch. In one embodiment, where both mannitol and starch are present in the dosage form, the dosage form comprises about 100 mg of starch, and the remaining weight is filled by starch. In one embodiment, the mannitol is spray dried mannitol. In another embodiment, the starch is pregelatinized starch.

In one embodiment where the total weight of the dosage form is about 180 mg and where a lubricant is present, the lubricant is sodium stearyl fumarate. In one embodiment, the sodium stearyl fumarate is present at an amount of about 0.5 mg. In one embodiment, the sodium stearyl fumarate is present at an amount of about 0.45 mg.

In one embodiment, provided herein is a dosage form comprising: 1) pomolidomide, or a pharmaceutically acceptable stereoisomer, prodrug, salt, solvate, or clathrate thereof, present at an amount that provides about 3 mg potency of pomolidomide; 2) about 100.8 mg of pregelatinized starch; 3) about 0.45 mg of sodium stearyl fumarate; and 4) spray dried mannitol at an amount that brings the total weight of the dosage form to 180 mg. In one embodiment, the dosage form is suitable for administration in a size 2 or larger capsule.

In one embodiment, provided herein is a dosage form comprising: 1) pomolidomide, or a pharmaceutically acceptable stereoisomer, prodrug, salt, solvate, or clathrate thereof, present at an amount that provides about 4 mg potency of pomolidomide; and 2) a pharmaceutically acceptable excipient. In one embodiment, the total weight of the dosage form is about 240 mg. In one embodiment, the dosage form is suitable for administration in a size 2 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 240 mg, the carrier, diluent, binder, or filler comprises mannitol and/or starch. In one embodiment, the excipient comprises both mannitol and starch. In one embodiment, where both mannitol and starch are present in the dosage form, the dosage form comprises about 135 mg of starch, and the remaining weight is filled by starch. In one embodiment, the mannitol is spray dried mannitol. In another embodiment, the starch is pregelatinized starch.

In one embodiment where the total weight of the dosage form is about 240 mg and where a lubricant is present, the lubricant is sodium stearyl fumarate. In one embodiment, the sodium stearyl fumarate is present at an amount of about 0.6 mg.

In one embodiment, provided herein is a dosage form comprising: 1) pomolidomide, or a pharmaceutically acceptable stereoisomer, prodrug, salt, solvate, or clathrate thereof, present at an amount that provides about 4 mg potency of pomolidomide; 2) about 134.4 mg of pregelatinized starch; 3) about 0.6 mg of sodium stearyl fumarate; and 4) spray dried mannitol at an amount that brings the total weight of the dosage form to 240 mg. In one embodiment, the dosage form is suitable for administration in a size 2 or larger capsule.

In one embodiment, provided herein is a dosage form comprising: 1) pomolidomide, or a pharmaceutically acceptable stereoisomer, prodrug, salt, solvate, or clathrate thereof, present at an amount that provides about 5 mg potency of pomolidomide; and 2) a pharmaceutically acceptable excipient. In one embodiment, the total weight of the dosage form is about 300 mg. In one embodiment, the dosage form is suitable for administration in a size 1 or larger capsule. In one embodiment, the excipient comprises a carrier, diluent, binder, or filler. In one embodiment, the excipients comprise a carrier, diluent, binder, or filler and a lubricant.

In one embodiment where the total weight of the dosage form is about 300 mg, the carrier, diluent, binder, or filler comprises mannitol and/or starch. In one embodiment, the excipient comprises both mannitol and starch. In one embodiment, where both mannitol and starch are present in the dosage form, the dosage form comprises about 168 mg of starch, and the remaining weight is filled by starch. In one embodiment, the mannitol is spray dried mannitol. In another embodiment, the starch is pregelatinized starch.

In one embodiment where the total weight of the dosage form is about 300 mg and where a lubricant is present, the lubricant is sodium stearyl fumarate. In one embodiment, the sodium stearyl fumarate is present at an amount of about 0.8 mg. In one embodiment, the sodium stearyl fumarate is present at an amount of about 0.75 mg.

In one embodiment, provided herein is a dosage form comprising: 1) pomolidomide, or a pharmaceutically acceptable stereoisomer, prodrug, salt, solvate, or clathrate thereof, present at an amount that provides about 5 mg potency of pomolidomide; 2) about 168 mg of pregelatinized starch; 3) about 0.75 mg of sodium stearyl fumarate; and 4) spray dried mannitol at an amount that brings the total weight of the dosage form to 300 mg. In one embodiment, the dosage form is suitable for administration in a size 1 or larger capsule.

In another embodiment, provided herein is a dosage form comprising pomolidomide, or a pharmaceutically acceptable stereoisomer, prodrug, salt, solvate, or clathrate thereof, present at an amount that provides about 0.5 mg potency of pomolidomide, which is stable for a period of at least about 12, about 24, or about 36 months without refrigeration. In some embodiments, the dosage form comprises mannitol and/or starch. In one embodiment where both starch and mannitol are present in the dosage form, starch is present at an amount of about 35 mg, and mannitol is present at an amount that brings the total weight of composition to about 62.5 mg. In some embodiments, the dosage form further comprises sodium stearyl fumarate at an amount of about 0.2 mg or about 0.16 mg. In some embodiments, provided herein is a dosage form comprising: 1) pomolidomide, or a pharmaceutically acceptable stereoisomer, prodrug, salt, solvate, or clathrate thereof, present at an amount that provides about 0.5 mg potency of pomolidomide, about 35 mg pregelatinized starch; about 0.16 mg sodium stearyl fumarate; and spray dried mannitol at an amount that brings the total weight of the dosage form to 62.5 mg; wherein the dosage form is stable for a period of at least about 12, about 24, or about 36 months without refrigeration. In one embodiment, the dosage form is suitable for administration in a size 4 or larger capsule.

In another embodiment, provided herein is a dosage form comprising pomolidomide, or a pharmaceutically acceptable stereoisomer, prodrug, salt, solvate, or clathrate thereof, present at an amount that provides about 1 mg potency of pomolidomide, which is stable for a period of at least about 12, about 24, or about 36 months without refrigeration. In some embodiments, the dosage form comprises mannitol and/or starch. In one embodiment where both starch and mannitol are present in the dosage form, starch is present at an amount of about 70 mg, and mannitol is present at an amount that brings the total weight of composition to about 125 mg. In some embodiments, the dosage form further comprises sodium stearyl fumarate at an amount of about 0.3 mg or about 0.32 mg. In some embodiments, provided herein is a dosage form comprising: 1) pomolidomide, or a pharmaceutically acceptable stereoisomer, prodrug, salt, solvate, or clathrate thereof, present at an amount that provides about 1 mg potency of pomolidomide, about 70 mg pregelatinized starch; about 0.32 mg sodium stearyl fumarate; and spray dried mannitol at an amount that brings the total weight of the dosage form to 125 mg; wherein the dosage form is stable for a period of at least about 12, about 24, or about 36 months without refrigeration. In one embodiment, the dosage form is suitable for administration in a size 4 or larger capsule.

In another embodiment, provided herein is a dosage form comprising pomolidomide, or a pharmaceutically acceptable stereoisomer, prodrug, salt, solvate, or clathrate thereof, present at an amount that provides about 2 mg potency of pomolidomide, which is stable for a period of at least about 12, about 24, or about 36 months without refrigeration. In some embodiments, the dosage form comprises mannitol and/or starch. In one embodiment where both starch and mannitol are present in the dosage form, starch is present at an amount of about 140 mg, and mannitol is present at an amount that brings the total weight of composition to about 250 mg. In some embodiments, the dosage form further comprises sodium stearyl fumarate at an amount of about 0.6 mg or about 0.64 mg. In some embodiments, provided herein is a dosage form comprising: 1) pomolidomide, or a pharmaceutically acceptable stereoisomer, prodrug, salt, solvate, or clathrate thereof, present at an amount that provides about 2 mg potency of pomolidomide, about 140 mg pregelatinized starch; about 0.64 mg sodium stearyl fumarate; and spray dried mannitol at an amount that brings the total weight of the dosage form to 250 mg; wherein the dosage form is stable for a period of at least about 12, about 24, or about 36 months without refrigeration. In one embodiment, the dosage form is suitable for administration in a size 2 or larger capsule.

In another embodiment, provided herein is a dosage form comprising pomolidomide, or a pharmaceutically acceptable stereoisomer, prodrug, salt, solvate, or clathrate thereof, present at an amount that provides about 5 mg potency of pomolidomide, which is stable for a period of at least about 12, about 24, or about 36 months without refrigeration. In some embodiments, the dosage form comprises mannitol and/or starch. In one embodiment where both starch and mannitol are present in the dosage form, starch is present at an amount of about 168 mg, and mannitol is present at an amount that brings the total weight of composition to about 300 mg. In some embodiments, the dosage form further comprises sodium stearyl fumarate at an amount of about 0.8 mg or about 0.75 mg. In some embodiments, provided herein is a dosage form comprising: 1) pomolidomide, or a pharmaceutically acceptable stereoisomer, prodrug, salt, solvate, or clathrate thereof, present at an amount that provides about 5 mg potency of pomolidomide, about 168 mg pregelatinized starch; about 0.75 mg sodium stearyl fumarate; and spray dried mannitol at an amount that brings the total weight of the dosage form to 300 mg; wherein the dosage form is stable for a period of at least 12, about 24, or about 36 months without refrigeration. In one embodiment, the dosage form is suitable for administration in a size 1 or larger capsule.

4.1.1 Second Active Agents

In certain embodiments, provided herein are compositions and dosage form of pomolidomide, or a pharmaceutically acceptable stereoisomer, prodrug, salt, solvate, or clathrate thereof, which may further comprise one or more secondary active ingredients.

Certain combinations may work synergistically in the treatment of particular types diseases or disorders, and conditions and symptoms associated with such diseases or disorders. Pomolidomide, or a pharmaceutically acceptable stereoisomer, prodrug, salt, solvate, or clathrate thereof, can also work to alleviate adverse effects associated with certain second active agents, and vice versa.

Specific second active compounds that can be contained in the formulations and dosage forms provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine;

dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Yet other second active agents include, but are not limited to, 2-methoxyestradiol, telomestatin, inducers of apoptosis in mutiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin)(Doxil®), paclitaxel, ganciclovir, adriamycin, estramustine sodium phosphate)(Emcyt®), sulindac, and etoposide.

In another embodiment, examples of specific second agents according to the indications to be treated, prevented, or managed can be found in the following references, all of which are incorporated herein in their entireties: U.S. Pat. Nos. 6,281,230 and 5,635,517; U.S. publication nos. 2004/0220144, 2004/0190609, 2004/0087546, 2005/0203142, 2004/0091455, 2005/0100529, 2005/0214328, 2005/0239842, 2006/0154880, 2006/0122228, and 2005/0143344; and U.S. provisional application No. 60/631,870.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate)(Aspirin®), celecoxib) (Celebrex®), Enbrel®, ketamine, gabapentin)(Neurontin®), phenytoin)(Dilantin®), carbamazepine (Tegretol®)), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

Examples of second active agents that may be used for the treatment, prevention and/or management of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof specific examples include, but are not limited to, verteporfin, purlytin, an angiostatic steroid, rhuFab, interferon-2α, pentoxifylline, tin etiopurpurin, motexafin, lucentis, lutetium, 9-fluoro-11,21-dihydroxy-16, 17-1-methylethylidinebis (oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of pulmonary hepertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin I2 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of second active agents that may be used for the treatment, prevention and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stibogluconate), interfereon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: opioids; a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; hydroxy urea; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

4.2. Process for Making Dosage Forms

Dosage forms provided herein can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent. Encapsulation of the dosage forms provided herein can be done using capsules of methylcellulose, calcium alginate, or gelatin.

In some embodiments, the active ingredients and excipients are directly blended and loaded into, for example, a capsule, or compressed directly into tablets. A direct-blended dosage form may be more advantageous than a compacted (e.g., roller-compacted) dosage form in certain instances, since direct-blending can reduce or eliminate the harmful health effects that may be caused by airborne particles of ingredients during the manufacture using compaction process.

Direct blend formulations may be advantageous in certain instances because they require only one blending step, that of the active and excipients, before being processed into the final dosage form, e.g., tablet or capsule. This can reduce the production of airborne particle or dust to a minimum, while roller-compaction processes may be prone to produce dust. In roller-compaction process, the compacted material is often milled into smaller particles for further processing. The milling operation can produce significant amounts of airborne particles, since the purpose for this step in manufacturing is to reduce the materials particle size. The milled material is then blended with other ingredients prior to manufacturing the final dosage form.

For certain active ingredients, in particular for a compound with a low solubility, the active ingredient's particle size is reduced to a fine powder in order to help increase the active ingredient's rate of solubilization. The increase in the rate of solubilization is often necessary for the active ingredient to be effectively absorbed in the gastrointestinal tract. However for fine powders to be directly-blended and loaded onto capsules, the excipients should preferably provide certain characteristics which render the ingredients suitable for the direct-blend process. Examples of such characteristics include, but are not limited to, acceptable flow characteristics. In one embodiment, therefore, provided herein is the use of, and compositions comprising, excipients which may provide characteristics, which render the resulting mixture suitable for direct-blend process, e.g., good flow characteristics.

4.2.1. Screening

The process for making the pharmaceutical compositions of the invention preferably includes the screening of the active ingredient and the excipient(s). In one embodiment, the active ingredient is passed through a screen having openings of about 200 microns to about 750 microns. In another embodiment, the active ingredient is passed through a screen with openings of about 200 microns to about 400 microns. In one embodiment, the active ingredient is passed through a screen having openings of about 300 to about 400 microns. Depending on the excipient(s) used, the screen openings vary. For example, disintegrants and binders are passed through openings of about 430 microns to about 750 microns, from about 600 microns to about 720 microns, or about 710 microns. Lubricants are typically passed through smaller openings, e.g., about 150 microns to about 250 microns screen. In one embodiment, the lubricant is passed through a screen opening of about 210 microns.

4.2.2. Pre-Blending

After the ingredients are screened, the excipient and active ingredient are mixed in a diffusion mixer. In one embodiment, the mixing time is from about 1 minute to about 50 minutes, from about 5 minutes to about 45 minutes, from about 10 minutes to about 40 minutes, or from about 10 minutes to about 25 minutes. In another embodiment, the mixing time is about 15 minutes.

When more than one excipients are used, the excipients may be admixed in a tumble blender for about 1 minute to about 20 minutes, or for about 5 minutes to about 10 minutes, prior to mixing with the active ingredient.

4.2.3. Roller Compaction

In one embodiment, the pre-blend may optionally be passed through a roller compactor with a hammer mill attached at the discharge of the compactor.

4.2.4. Final Blend

When a lubricant, e.g., sodium stearyl fumarate, is used, the lubricant is mixed with the pre-blend at the end of the process to complete the pharmaceutical composition. This additional mixing is from about 1 minute to about 10 minutes, or from about 3 minutes to about 5 minutes.

4.2.5. Encapsulation

The formulation mixture is then encapsulated into the desired size capsule shell using, for example, a capsule filling machine or a rotary tablet press.

4.3. Kits

Pharmaceutical packs or kits which comprise pharmaceutical compositions or dosage forms provided herein are also provided. An example of a kit comprises notice in the form prescribed by a governmental agency regulating the manufacture, use or sale of pharmaceuticals or biological products, which notice reflects approval by the agency of manufacture, use or sale for human administration.

4.4. Methods of Treatment, Prevention, and Management

Provided herein are methods of treating, preventing, and/or managing certain diseases or disorders using the formulations, compositions, or dosage forms provided herein.

Examples of diseases or disorders include, but are not limited to, cancer, disorders associated with angiogenesis, pain including, but not limited to, Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), TNFα related disorders, and other various diseases and disorders.

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Certain examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing or managing either primary or metastatic tumors.

Other cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

In one embodiment, the diseases or disorders are various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another embodiment, the diseases or disorders are various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), follicular lymphoma, and any type of the mantle cell lymphomas that can be seen under the microscope (nodular, diffuse, blastic and mentle zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent publication no. 2005/0203142, published Sep. 15, 2005, which is incorporated herein by reference. Specific types of pain include, but are not limited to, nociceptive pain, neuropathic pain, mixed pain of nociceptive and neuropathic pain, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of MD and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, those described in U.S. publication no. 2005/0214328A1, published Sep. 29, 2005, which is incorporated herein by reference. Specific examples include, but are not limited to, keratoses and related symptoms, skin diseases or disorders characterized with overgrowths of the epidermis, acne, and wrinkles.

As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trélat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. publication no. 2005/0239842A1, published Oct. 27, 2005, which is incorporated herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but not limited to, those described in U.S. publication no. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. publication no. 2006/0154880, published Jul. 13, 2006, which is incorporated herein by reference. Parasitic diseases include diseases and disorders caused by human intracellular parasites such as, but not limited to, *P. falcifarium, P. ovale, P. vivax, P. malariae, L. donovari, L. infantum, L. aethiopica, L. major, L. tropica, L. mexicana, L. braziliensis, T. Gondii, B. microti, B. divergens, B. coli, C. parvum, C. cayetanensis, E. histolytica, I. belli, S. mansonii, S. haematobium, Trypanosoma* ssp., *Toxoplasma* ssp., and *O. volvulus*. Other diseases and disorders caused by non-human intracellular parasites such as, but not limited to, *Babesia bovis, Babesia canis, Banesia Gibsoni, Besnoitia darlingi, Cytauxzoon felis, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. application Ser. No. 11/289,723, filed Nov. 30, 2005. Specific examples include, but not limited to, adenosine deaminase deficiency, antibody deficiency with normal or elevated Igs, ataxia-tenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. publication no. 2005/0143344, published Jun. 30, 2005, which is incorporated herein by reference. Specific examples include, but are not limited to, include, but are not limited to, Amyotrophic Lateral Sclerosis, Alzheimer Disease, Parkinson Disease, Huntington's Disease, Multiple Sclerosis other neuroimmunological disorders such as Tourette Syndrome, delerium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. publication no. 2006/0122228, published Jun. 8, 2006, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but not limited to, viral, genetic, allergic, and autoimmune diseases. Specific examples include, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythematosus, ENL in leprosy, radiation damage, cancer, asthma, or hyperoxic alveolar injury.

Examples of atherosclerosis and related conditions include, but are not limited to, those disclosed in U.S. publication no. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated herein, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary by-pass grafting, angioplasty with stent implantation, peripheral percutaneous transluminal intervention of the iliac, femoral or popliteal arteries, and surgical intervention using impregnated artificial grafts. The following chart provides a listing of the major systemic arteries that may be in need of treatment, all of which are contemplated herein:

| Artery | Body Areas Supplied |
| --- | --- |
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |
| Internal iliac | Rectum, urinary bladder, external genitalia, buttocks muscles, uterus and vagina |
| Left gastric | Esophagus and stomach |
| Middle sacral | Sacrum |
| Ovarian | Ovaries |
| Palmar arch | Hand |
| Peroneal | Calf |
| Popliteal | Knee |
| Posterior tibial | Calf |
| Pulmonary | Lungs |
| Radial | Forearm |
| Renal | Kidney |
| Splenic | Stomach, pancreas, and spleen |
| Subclavian | Shoulder |
| Superior mesenteric | Pancreas, small intestine, ascending and transverse colon |
| Testicular | Testes |
| Ulnar | Forearm |

Examples of dysfunctional sleep and related syndromes include, but are not limited to, those disclosed in U.S. publication no. 2005/0222209A1, published Oct. 6, 2005, which is incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. publication no. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis, psoriatic arthritis and other arthritic conditions, septic shock, septis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In other embodiments, the use of formulations, compositions or dosage forms provided herein in various immunological applications, in particular, as vaccine adjuvants, particularly anticancer vaccine adjuvants, as disclosed in U.S. Publication No. 2007/0048327, published Mar. 1, 2007, which is incorporated herein in its entirety by reference, is also encompassed. These embodiments also relate to the uses of the compositions, formulations, or dosage forms provided herein in combination with vaccines to treat or prevent cancer or infectious diseases, and other various uses such as reduction or desensitization of allergic reactions.

5. EXAMPLES

Embodiments provided herein may be more fully understood by reference to the following examples. These examples are meant to be illustrative of pharmaceutical compositions and dosage forms provided herein, but are not in any way limiting.

5.1 Example 1: 0.5 mg Strength Pomolidomide Dosage Capsule

Table 1 illustrates a batch formulation and single dosage formulation for a 0.5 mg strength pomolidomide single dose unit in a size #4 capsule.

TABLE 1

Formulation for 0.5 mg strength pomolidomide capsule

| Material | Percent By Weight | Quantity (mg/capsule) |
|---|---|---|
| Pomolidomide | ~1% | 0.5* |
| Starch 1500 | 56% | 35 |
| Sodium Stearyl Fumarate (PRUV) | ~0.3% | 0.16 |
| Spray Dried Mannitol (Mannogem EZ) | remainder | remainder |
| Total | 100.0% | 62.5 |

*Denotes amount of pomolidomide that corresponds to the amount that provides the potency of 0.5 mg of pomolidomide.

Pomolidomide was passed through a 35-mesh screen. Mannitol and starch were each separately passed through a 25-mesh screen. Pomolidomide was pre-blended with a portion of mannitol and starch. The pre-blend was milled through a 0.039 inch screen. The remainder of the mannitol and starch was also milled through a 0.039 inch screen. The pre-blend was blended with the reminder of mannitol and starch. To this blend, sodium fumarate, which was passed through a 60 mesh screen, was further blended. The final blend was encapsulated into a size #4 capsule.

5.2 Example 2: 1 mg Strength Pomolidomide Dosage Capsule

Table 2 illustrates a batch formulation and single dosage formulation for a 1 mg strength pomolidomide single dose unit in a size #4 capsule.

TABLE 2

Formulation for 1 mg strength pomolidomide capsule

| Material | Percent By Weight | Quantity (mg/capsule) |
|---|---|---|
| Pomolidomide | ~1% | 1* |
| Starch 1500 | 56% | 70 |
| Sodium Stearyl Fumarate (PRUV) | ~0.3% | 0.32 |
| Spray Dried Mannitol (Mannogem EZ) | remainder | remainder |
| Total | 100.0% | 125 |

*Denotes amount of pomolidomide that corresponds to the amount that provides the potency of 1 mg of pomolidomide.

Pomolidomide was passed through a 35-mesh screen. Mannitol and starch were each separately passed through a 25-mesh screen. Pomolidomide was pre-blended with a portion of mannitol and starch. The pre-blend was milled through a 0.039 inch screen. The remainder of the mannitol and starch was also milled through a 0.039 inch screen. The pre-blend was blended with the reminder of mannitol and starch. To this blend, sodium fumarate, which was passed through a 60 mesh screen, was further blended. The final blend was encapsulated into a size #4 capsule.

5.3 Example 3: 2 mg Strength Pomolidomide Dosage Capsule

Table 3 illustrates a batch formulation and single dosage formulation for a 2 mg pomolidomide single dose unit in a size #2 capsule.

TABLE 3

Formulation for 2 mg strength pomolidomide capsule

| Material | Percent By Weight | Quantity (mg/capsule) |
|---|---|---|
| Pomolidomide | ~1% | 2* |
| Starch 1500 | 56% | 140 |
| Sodium Stearyl Fumarate (PRUV) | ~0.3% | 0.64 |
| Spray Dried Mannitol (Mannogem EZ) | remainder | remainder |
| Total | 100.0% | 250 |

*Denotes amount of pomolidomide that corresponds to the amount that provides the potency of 2 mg of pomolidomide.

Pomolidomide was passed through a 35-mesh screen. Mannitol and starch were each separately passed through a 25-mesh screen. Pomolidomide was pre-blended with a portion of mannitol and starch. The pre-blend was milled through a 0.039 inch screen. The remainder of the mannitol and starch was also milled through a 0.039 inch screen. The pre-blend was blended with the reminder of mannitol and starch. To this blend, sodium fumarate, which was passed through a 60 mesh screen, was further blended. The final blend was encapsulated into a size #2 capsule.

5.4 Example 4: 3 mg Strength Pomolidomide Dosage Capsule

Table 4 illustrates a batch formulation and single dosage formulation for a 0.5 mg strength pomolidomide single dose unit in a size #2 capsule.

TABLE 4

Formulation for 3 mg strength pomolidomide capsule

| Material | Percent By Weight | Quantity (mg/capsule) |
|---|---|---|
| Pomolidomide | ~1.6% | 3* |
| Starch 1500 | 56% | 100.8 |
| Sodium Stearyl Fumarate (PRUV) | ~0.3% | 0.45 |
| Spray Dried Mannitol (Mannogem EZ) | remainder | remainder |
| Total | 100.0% | 180 |

*Denotes amount of pomolidomide that corresponds to the amount that provides the potency of 3 mg of pomolidomide.

Pomolidomide was passed through a 35-mesh screen. Mannitol and starch were each separately passed through a 25-mesh screen. Pomolidomide was pre-blended with a portion of mannitol and starch. The pre-blend was milled through a 0.039 inch screen. The remainder of the mannitol and starch was also milled through a 0.039 inch screen. The pre-blend was blended with the reminder of mannitol and starch. To this blend, sodium fumarate, which was passed through a 60 mesh screen, was further blended. The final blend was encapsulated into a size #2 capsule.

5.5 Example 5: 4 mg Strength Pomolidomide Dosage Capsule

Table 5 illustrates a batch formulation and single dosage formulation for a 0.5 mg strength pomolidomide single dose unit in a size #2 capsule.

TABLE 5

Formulation for 4 mg strength pomolidomide capsule

| Material | Percent By Weight | Quantity (mg/capsule) |
|---|---|---|
| Pomolidomide | ~1.6% | 4* |
| Starch 1500 | 56% | 134.4 |
| Sodium Stearyl Fumarate (PRUV) | ~0.3% | 0.6 |
| Spray Dried Mannitol (Mannogem EZ) | remainder | remainder |
| Total | 100.0% | 240 |

*Denotes amount of pomolidomide that corresponds to the amount that provides the potency of 4 mg of pomolidomide.

Pomolidomide was passed through a 35-mesh screen. Mannitol and starch were each separately passed through a 25-mesh screen. Pomolidomide was pre-blended with a portion of mannitol and starch. The pre-blend was milled through a 0.039 inch screen. The remainder of the mannitol and starch was also milled through a 0.039 inch screen. The pre-blend was blended with the reminder of mannitol and starch. To this blend, sodium fumarate, which was passed through a 60 mesh screen, was further blended. The final blend was encapsulated into a size #2 capsule.

5.6 Example 6: 5 mg Strength Pomolidomide Dosage Capsule

Table 6 illustrates a batch formulation and single dosage formulation for a 5 mg pomolidomide single dose unit in a size #1 capsule.

TABLE 4

Formulation for 5 mg strength pomolidomide capsule

| Material | Percent By Weight | Quantity (mg/capsule) |
|---|---|---|
| Pomolidomide | ~2% | 5* |
| Starch 1500 | 56% | 168 |
| Sodium Stearyl Fumarate (PRUV) | ~0.3% | 0.75 |
| Spray Dried Mannitol (Mannogem EZ) | remainder | remainder |
| Total | 100.0% | 300 |

*Denotes amount of pomolidomide that corresponds to the amount that provides the potency of 5 mg of pomolidomide.

Pomolidomide was passed through a 35-mesh screen. Mannitol and starch were each separately passed through a 25-mesh screen. Pomolidomide was pre-blended with a portion of mannitol and starch. The pre-blend was milled through a 0.039 inch screen. The remainder of the mannitol and starch was also milled through a 0.039 inch screen. The pre-blend was blended with the reminder of mannitol and starch. To this blend, sodium fumarate, which was passed through a 60 mesh screen, was further blended. The final blend was encapsulated into a size #1 capsule.

5.7 Example 7: Stability of Formulation

Accelerated stability was assessed under 40° C./75% RH, and levels of impurities over the time period of initial, 1 month, 3 months, and 6 months were determined. Long term stability under 25° C./60% RH is also assessed during 0-24 months. For determination of the level of impurities, an HPLC gradient method was employed using the following conditions:

Column: Zorbax SB-CN, 150 mm×4.6 mm id, 5 µm particle size
Temperature: Ambient
Mobile Phase: A: 10/90 methanol/0.1% trifluoroacetic acid
B: 80/20 methanol/0.1% trifluoroacetic acid

| Gradient Profile: | Time (min) | % A | % B |
|---|---|---|---|
| | 0 | 90 | 10 |
| | 5 | 90 | 10 |
| | 50 | 20 | 80 |
| | 51 | 90 | 10 |
| | 60 | 90 | 10 |

Flow Rate: 1.0 mL/min
Injection Volume: 25 µL
Detection: UV, 240 nm
Run Time: 60 minutes.

From the experiments, it was observed that the impurities in the formulation provided herein stayed negligent throughout the time period investigated. The performance characteritics of the dosage also maintained throughout the time period investigated. These results show that the formulations provided herein have adequate stability for clinical and other uses.

While examples of certain particular embodiments are provided herein, it will be apparent to those skilled in the art that various changes and modifications may be made. Such modifications are also intended to fall within the scope of the appended claims.

What is claimed is:

1. An oral dosage form in the form of a capsule which comprises: 1) pomolidomide at an amount of 0.1 to 3 weight percent of the total weight of the composition; 2) a binder or filler at an amount of 70 to 99 weight percent of total weight of the composition, wherein the binder or filler is a mixture of mannitol and starch; and wherein the ratio of mannitol:starch in the dosage form is from about 1:1 to about 1:1.5.

2. The oral dosage form of claim 1, wherein pomolidomide is present at an amount of 0.5 to 2 weight percent of total weight of the composition.

3. The oral dosage form of claim 1, wherein the binder or filler is present at an amount of 85 to 99 weight percent of total weight of the composition.

4. The oral dosage form of claim 1, wherein the starch is pregelatinized starch.

5. The oral dosage form of claim 1, wherein the mannitol is spray dried mannitol.

6. The oral dosage form of claim 1 further comprising a lubricant at an amount of 0.01 to 1 weight percent of total weight of the composition.

7. The oral dosage form of claim 6, wherein the lubricant is present at an amount of 0.1 to 0.5 weight percent of total weight of the composition.

8. The oral dosage form of claim 7, wherein the lubricant is sodium stearyl fumarate.

* * * * *